(12) United States Patent
Russo et al.

(10) Patent No.: US 9,402,634 B2
(45) Date of Patent: Aug. 2, 2016

(54) DEVICE AND METHOD FOR TREATING VASCULAR ABNORMALITIES

(71) Applicant: AGA Medical Corporation, Plymouth, MN (US)

(72) Inventors: Patrick Russo, Vadnais Heights, MN (US); John Oslund, Blaine, MN (US); Matthew C. Heidner, Maple Grove, MN (US); Jessica Akers, Cambridge, MA (US)

(73) Assignee: ST. JUDE MEDICAL, CARDIOLOGY DIVISION, INC., St. Paul, MN (US)

( * ) Notice: Subject to any disclaimer, the term of this patent is extended or adjusted under 35 U.S.C. 154(b) by 283 days.

(21) Appl. No.: 14/090,820

(22) Filed: Nov. 26, 2013

(65) Prior Publication Data

US 2014/0088635 A1    Mar. 27, 2014

Related U.S. Application Data

(62) Division of application No. 13/236,763, filed on Sep. 20, 2011, now Pat. No. 8,621,975.

(51) Int. Cl.
*A61F 2/06* (2013.01)
*A61B 17/12* (2006.01)
(Continued)

(52) U.S. Cl.
CPC ........... *A61B 17/12109* (2013.01); *A61F 2/852* (2013.01); *A61F 2/90* (2013.01); *B21F 45/008* (2013.01); *A61F 2/07* (2013.01); *A61F 2210/0076* (2013.01);
(Continued)

(58) Field of Classification Search
None
See application file for complete search history.

(56) References Cited

U.S. PATENT DOCUMENTS

| 4,655,771 A | 4/1987 | Wallsten |
| 4,728,328 A | 3/1988 | Hughes et al. |

(Continued)

FOREIGN PATENT DOCUMENTS

| EP | 2143404 A1 | 1/2010 |
| WO | 9532757 A1 | 12/1995 |

(Continued)

OTHER PUBLICATIONS

International Search Report and Written Opinion of the Search Authority for Application No. PCT/US2012055721; dated Nov. 27, 2012.

(Continued)

*Primary Examiner* — Tuan V Nguyen
(74) *Attorney, Agent, or Firm* — Armstrong Teasdale LLP

(57) ABSTRACT

A vascular device is provided that includes a tubular structure and an occluding structure. The tubular structure has inner and outer layers, with the occluding structure located between the inner and outer layers. Each of the inner and outer layers may define a different pick count, and the tubular structure may include a leading edge at a transition between the pick counts. The leading edge may be disposed at the distal end of the vascular device when the device is deployed from a delivery device. Furthermore, the occluding structure may have first and second layers formed by the inversion or eversion of the occluding structure and the subsequent coupling of its free ends to form a continuous structure. Thus, any loose ends may be sealed to minimize unraveling and/or shifting of the occluding structure within the tubular structure. A method of making the vascular device is also provided.

20 Claims, 12 Drawing Sheets

(51) Int. Cl.
*A61F 2/24* (2006.01)
*A61F 2/852* (2013.01)
*A61F 2/90* (2013.01)
*B21F 45/00* (2006.01)
*A61F 2/07* (2013.01)

(52) U.S. Cl.
CPC *A61F 2220/0075* (2013.01); *A61F 2230/0067* (2013.01); *A61F 2250/0017* (2013.01); *A61F 2250/0048* (2013.01); *A61F 2250/0063* (2013.01)

(56) References Cited

U.S. PATENT DOCUMENTS

| | | |
|---|---|---|
| 4,954,126 A | 9/1990 | Wallsten |
| 5,064,435 A | 11/1991 | Porter |
| 5,522,881 A | 6/1996 | Lentz |
| 5,628,788 A | 5/1997 | Pinchuk |
| 5,645,559 A | 7/1997 | Hachtman et al. |
| 5,646,559 A | 7/1997 | Higurashi |
| 5,667,523 A | 9/1997 | Bynon et al. |
| 5,741,325 A | 4/1998 | Chaikof et al. |
| 5,758,562 A | 6/1998 | Thompson |
| 5,800,508 A | 9/1998 | Goicoechea et al. |
| 5,824,042 A | 10/1998 | Lombardi et al. |
| 5,824,055 A | 10/1998 | Spiridigliozzi et al. |
| 5,860,998 A | 1/1999 | Robinson et al. |
| 5,916,264 A | 6/1999 | Von Oepen et al. |
| 5,957,974 A | 9/1999 | Thompson et al. |
| 6,096,052 A | 8/2000 | Callister et al. |
| 6,110,198 A | 8/2000 | Fogarty et al. |
| 6,123,715 A | 9/2000 | Amplatz |
| 6,156,064 A | 12/2000 | Chouinard |
| 6,221,099 B1 | 4/2001 | Andersen et al. |
| 6,264,689 B1 | 7/2001 | Colgan et al. |
| 6,299,636 B1 | 10/2001 | Schmitt et al. |
| 6,500,203 B1 | 12/2002 | Thompson et al. |
| 6,613,078 B1 | 9/2003 | Barone |
| 6,709,451 B1 | 3/2004 | Noble et al. |
| 6,932,837 B2 | 8/2005 | Amplatz et al. |
| 6,978,643 B2 | 12/2005 | Akers et al. |
| 7,175,655 B1 | 2/2007 | Molaei |
| 7,473,271 B2 | 1/2009 | Gunderson |
| 7,942,924 B1 | 5/2011 | Perez et al. |
| 8,114,147 B2 | 2/2012 | Wood et al. |
| 8,163,004 B2 | 4/2012 | Amplatz et al. |
| 8,182,522 B2 | 5/2012 | Sarac et al. |
| 8,621,975 B2 * | 1/2014 | Russo ............... A61F 2/852 87/11 |
| 2003/0135265 A1 | 7/2003 | Stinson |
| 2006/0229697 A1 | 10/2006 | Gerdts et al. |
| 2006/0253184 A1 | 11/2006 | Amplatz |
| 2007/0106211 A1 | 5/2007 | Provost-Tine et al. |
| 2007/0118207 A1 | 5/2007 | Amplatz et al. |
| 2007/0168018 A1 | 7/2007 | Amplatz et al. |
| 2007/0168019 A1 | 7/2007 | Amplatz et al. |
| 2007/0265656 A1 | 11/2007 | Amplatz et al. |
| 2008/0281398 A1 | 11/2008 | Koss et al. |
| 2008/0288043 A1 | 11/2008 | Kaufmann et al. |
| 2009/0036966 A1 | 2/2009 | O'Connor et al. |
| 2009/0112251 A1 | 4/2009 | Qian et al. |
| 2009/0171427 A1 | 7/2009 | Melsheimer et al. |
| 2009/0210047 A1 | 8/2009 | Amplatz et al. |
| 2009/0210048 A1 | 8/2009 | Amplatz et al. |
| 2009/0312834 A1 | 12/2009 | Wood et al. |
| 2010/0023046 A1 | 1/2010 | Heidner et al. |
| 2010/0023048 A1 | 1/2010 | Mach |
| 2010/0106235 A1 | 4/2010 | Kariniemi et al. |
| 2011/0029059 A1 * | 2/2011 | Christiansen ............. A61F 2/07 623/1.2 |
| 2012/0150277 A1 | 6/2012 | Wood et al. |

FOREIGN PATENT DOCUMENTS

| | | |
|---|---|---|
| WO | 2006014233 A2 | 2/2006 |
| WO | 2011094527 A1 | 8/2011 |

OTHER PUBLICATIONS

International Search Report and Written Opinion for Application No. PCT/US2012/055718 dated Mar. 8, 2013.

International Search Report for Application No. PCT/US2012/055718; dated Nov. 23, 2012.

* cited by examiner

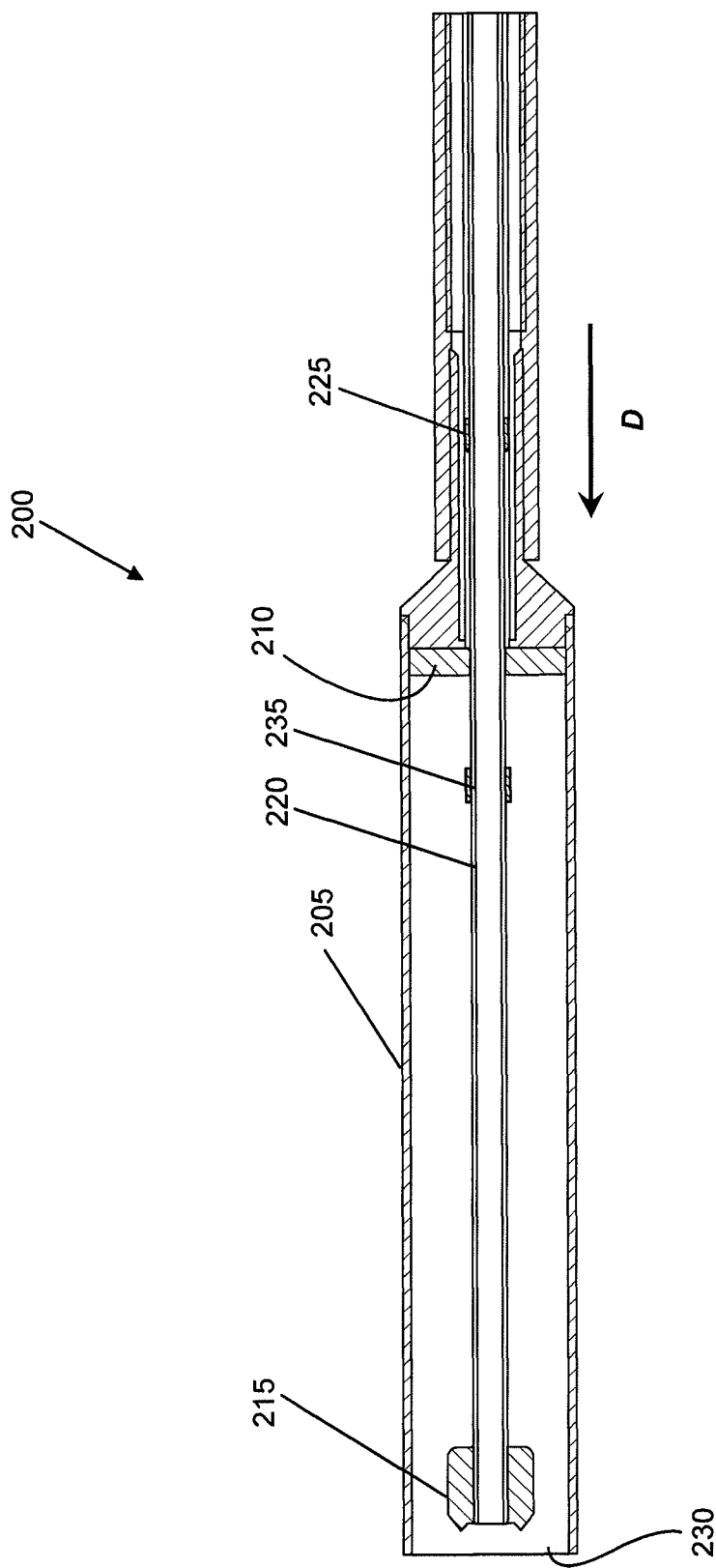

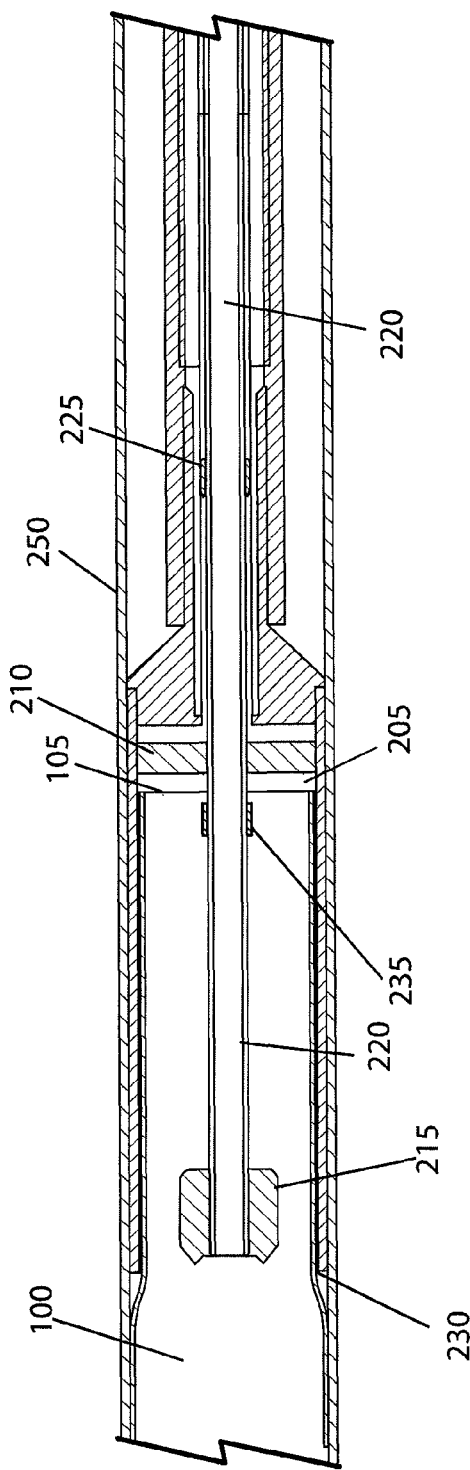
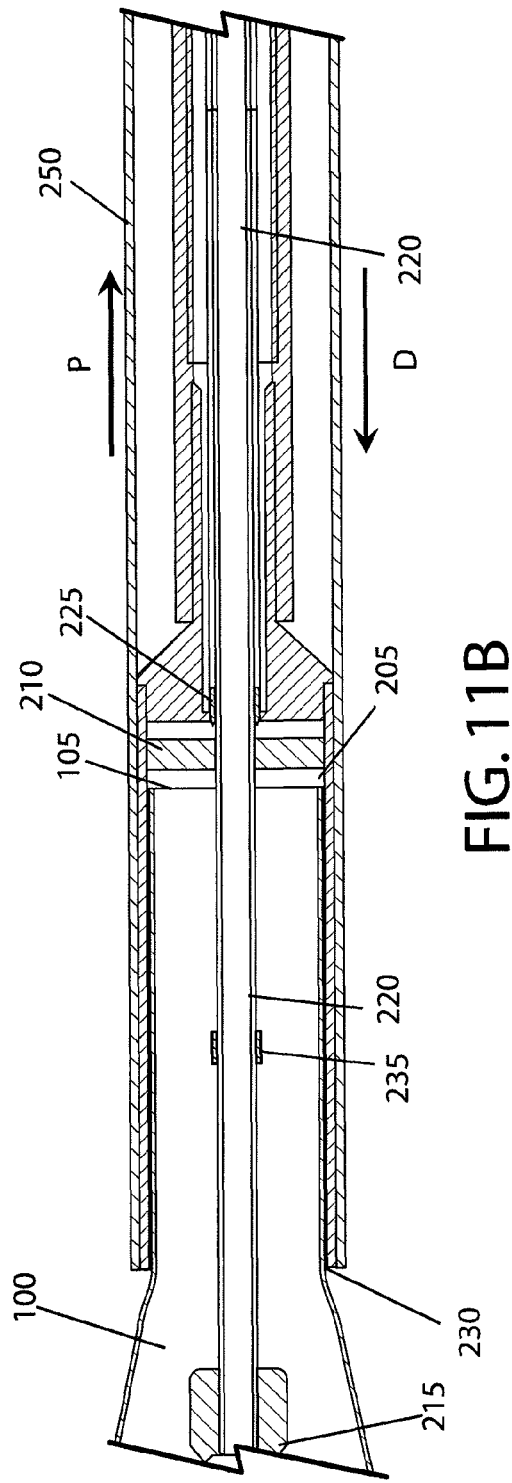
FIG.11A
FIG.11B

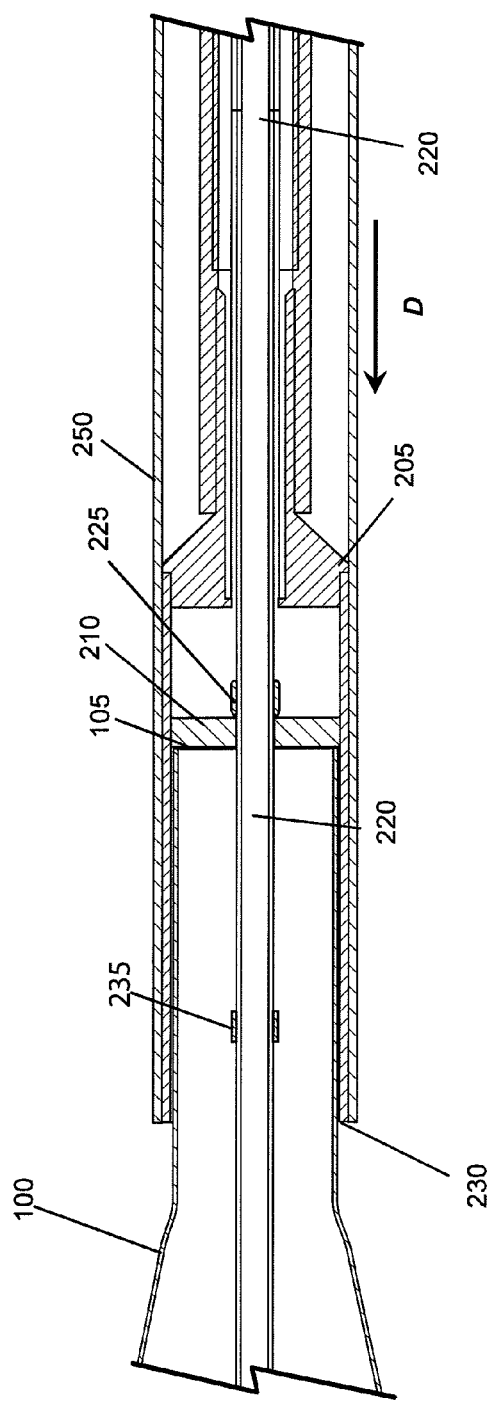
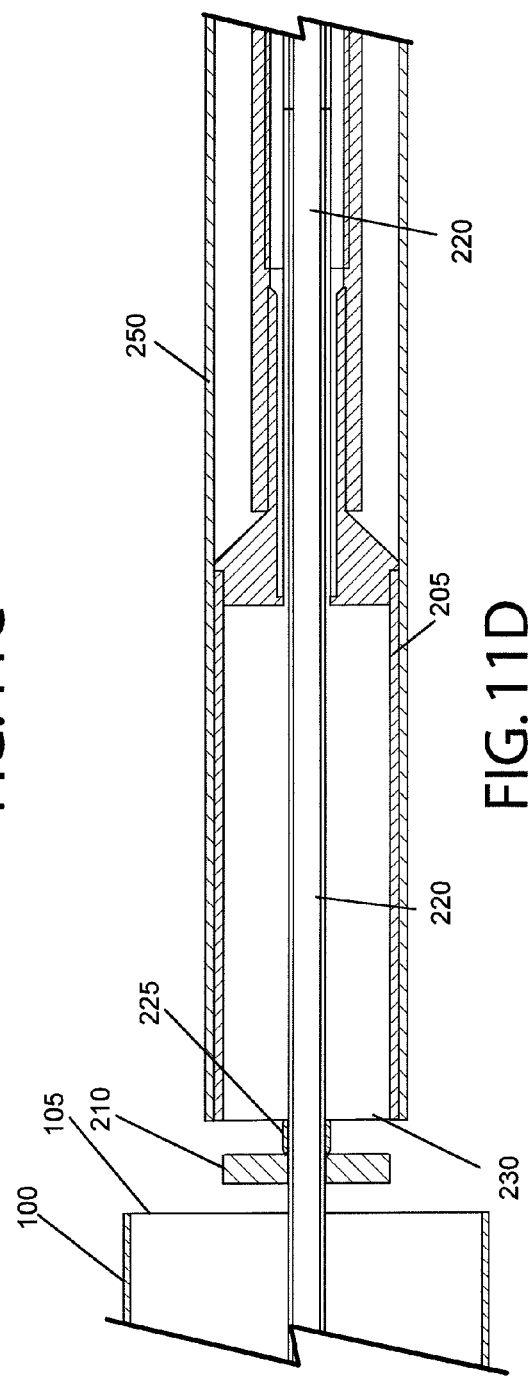
FIG. 11C
FIG. 11D

DEVICE AND METHOD FOR TREATING VASCULAR ABNORMALITIES

This application is a divisional of application Ser. No. 13/236,763 filed on Sep. 20, 2011, issued on Jan. 7, 2014 as U.S. Pat. No. 8,621,975, the disclosure of which is expressly incorporated herein by reference.

BACKGROUND

I. Field of the Invention

Embodiments of the present invention relate generally to vascular devices for treating certain vascular abnormalities, such as aneurysms. In particular, embodiments are directed to vascular devices including stents, grafts, and stent-grafts and methods for making vascular devices having a low profile for delivery and deployment in a patient's vasculature, such as the vessels of the thoracic area.

II. Description of the Related Art

Stents and grafts, both biological and synthetic, have been used for a large array of reparative vascular procedures, such as to treat obstructive vessels and aneurysms. An aortic aneurysm, for example, is a weakened, enlarged area in the aorta, which is the main blood vessel that carries blood from the heart to the rest of the body. Weaknesses in the aortic wall may be caused by medical conditions, such as arteriosclerosis. As blood flows through the aorta, the weak vessel wall thins over time and expands like a balloon, which can eventually burst if the vessel wall gets too thin.

Once an aortic aneurysm reaches about 5 cm in diameter, it is usually considered necessary to treat the aneurysm in an effort to prevent it from rupturing. Below 5 cm, the risk of the aneurysm rupturing is lower than the risk of conventional heart surgery in patients with normal surgical risks. The goal of therapy for aneurysms is to prevent the aorta from rupturing. Once an aortic aneurysm has ruptured, the chances of survival are low. Death may be avoided, however, if the aneurysm is detected and treated at an early stage, ideally when the aneurysm is smaller than about 5 cm, using a lower risk procedure.

Aneurysms may be treated with surgery. The surgical procedure for treating some types of aortic aneurysms involves replacing the affected portion of the aorta with a synthetic graft, which may comprise a tube made out of an elastomer or polymer material with properties that are intended to substitute the function of a normal, healthy aorta. Surgical treatment is complex, however, and may pose additional risks to the patient, especially the elderly.

More recently, instead of performing surgery to repair an aneurysm, an endovascular stent-graft may be delivered to the site of the aneurysm using elongated catheters. An endovascular stent-graft is a tube that includes a blood-impervious fabric supported by a metal mesh. It can be used to treat a variety of conditions involving blood vessels, but most commonly is used to reinforce a vessel wall at the site of an aneurysm.

To deliver a stent-graft to a target site in a patient's vasculature, typically, the surgeon will make a small incision in the patient's groin area and then insert a delivery catheter into the vasculature. The delivery catheter usually contains a collapsed, self-expanding or balloon-expandable stent-graft, which is configured to expand to approximately the normal diameter of the aorta at the location of the aneurysm or other abnormality once the stent-graft is deployed from the distal end of the delivery catheter. Over time, the stent-graft may become endothelialized, and the space between the outer wall of the stent-graft and the aneurysm should fill with clotted blood, preventing the aneurysm from growing further due to the stent-graft effectively bypassing (excluding) the aneurysm and prohibiting blood pressure and flow on the weakened segment of the patient's vasculature.

Depending on where the aneurysm is in relation to other branch vessels, different stent-graft design variations may be needed, for example, to avoid excluding blood flow through arteries that branch off from the aorta near the target site. Moreover, the stent-graft should be anchored within the lumen to reduce the incidence of migration, such as by promoting endothelialization or fixation with the vessel. Another consideration is the occurrence of endoleaks as a result of blood flowing around the stent, which may cause further weakening of the vessel wall at the site of the aneurysm.

Furthermore, the size of the delivery catheter may affect the ability of the surgeon to manipulate the catheter within the patient's vasculature. For example, when the aneurysm is located in a vessel having a small diameter and/or when the vessel diameter is reduced in size due to arteriosclerosis, larger delivery catheters may not be used or, at best, may result in trauma to the vascular tissue. Thus, the smaller the delivery catheter, the less tissue trauma should result and the easier it should be to accurately deliver the stent-graft at the proper location. Smaller delivery catheters also typically allow a physician to access smaller vessels, so as to more proactively treat aneurysms in a larger patient population.

Accordingly, there is a need for an improved vascular graft that is capable of being deployed using smaller-diameter delivery devices, is flexible for delivery through tortuous sections of vasculature, provides effective and rapid exclusion at the target site, is able to maintain its vascular position, and overcomes the shortcomings of conventional solutions.

SUMMARY OF THE INVENTION

Embodiments therefore provide a vascular device and method for making the same for deployment within a body lumen of a patient. In general, the vascular device may include a tubular structure comprising an inner layer and an outer layer. The vascular device may be configured such that the inner and outer layers experience relatively little movement with respect to each other as the device moves between a contracted state when constrained within a delivery device and an expanded state when deployed from the delivery device for delivery to a target site within the vessel lumen. In some cases, the inner and outer layers may have free ends proximate a proximal end of the vascular device and may be continuous at a distal end of the vascular device. Furthermore, the tubular structure may include a leading edge at a transition between the inner and outer layers. The leading edge may be configured to provide for accurate delivery to a target site and proper fixation to the luminal wall and may provide a low profile of the vascular device, especially near the distal end of the vascular device.

In one embodiment, a vascular device is provided that is configured to move between a contracted state when constrained within a delivery device and an expanded state when deployed from the delivery device for delivery to a target site within the body lumen. The vascular device may include a proximal end and a distal end and may comprise a tubular structure comprising an inner layer and an outer layer, wherein the inner layer defines a first pick count and the outer layer defines a second pick count. The inner layer of the tubular structure may be continuously braided with the outer layer of the tubular structure, and the first pick count, as braided, may be different from the second pick count, as braided. The first and second pick counts may be selected such that the relationship between the reduction in diameter and the elongation of the inner layer is substantially the same as the relationship between the reduction in diameter and the elongation of the outer layer as the vascular device is moved between the expanded state and the contracted state.

In some cases, the tubular structure may comprise a leading edge at a transition between the first pick count and the second pick count, and the leading edge may be disposed proximate the distal end of the vascular device when the vascular device is in the expanded state. The leading edge may be disposed within an interior of the vascular device when the vascular device is in the contracted state and may be configured to move to the distal end as the vascular device is deployed from the delivery device. Furthermore, each of the inner and outer layers of the tubular structure may comprise a free end proximate the proximal end of the vascular device. The first pick count, as braided, may be higher than the second pick count, as braided.

The vascular device may further comprise an occluding structure disposed between the inner and outer layers of the tubular structure. The occluding structure may be tubular in shape and may comprise a first layer and a second layer disposed between the inner and outer layers of the tubular structure. The first and second layers of the occluding structure may form a continuous structure via a coupling of free ends of the occluding structure, and the coupled free ends may be disposed adjacent the inner layer of the tubular structure. In some cases, the occluding structure may be attached to at least one of the inner layer or the outer layer of the tubular structure. The occluding structure may comprise a polymer material. Furthermore, the occluding structure may extend substantially from the distal end of the vascular device substantially to the proximal end of the vascular device. The outer layer of the tubular structure may include a section of increased thickness configured to maintain the vascular device within a delivery device prior to deployment. Also, in the expanded state, the inner layer of the tubular structure may define a length that is greater than a length defined by the outer layer of the tubular structure.

In some embodiments, a method of making a vascular device for placement in a body lumen is provided. The method may include braiding a tubular structure including a proximal portion and a distal portion, wherein the proximal portion defines a first pick count and the distal portion defines a second pick count, the first pick count being different than the second pick count. The method may further include folding the tubular structure onto itself such that a surface of the proximal portion of the tubular structure is adjacent a surface of the distal portion of the tubular structure to form an inner layer and an outer layer. After being folded, the relationship between the reduction in diameter and the elongation of the inner layer may be substantially the same as the relationship between the reduction in diameter and the elongation of the outer layer as the vascular device is moved between an expanded state and a contracted state.

The step of folding the tubular structure onto itself may comprise defining a leading edge at a transition between the first pick count and the second pick count. In some cases, the method may further comprise heat setting the tubular structure proximate the transition. The second pick count may be lower than the first pick count, and the step of folding the tubular structure onto itself may comprise everting the tubular structure, such that the distal portion forms the outer layer. Alternatively, the second pick count may be higher than the first pick count, and the step of folding the tubular structure onto itself may comprise inverting the tubular structure, such that the distal portion forms the inner layer.

In some embodiments, the method may further comprise placing an occluding structure between the inner and outer layers of the tubular structure. The occluding structure may be attached to at least one of the inner layer of the tubular structure or the outer layer of the tubular structure. In some cases, a section of increased thickness may be formed proximate a distal end of the outer layer of the tubular structure. The method may further comprise folding the occluding structure onto itself and coupling the ends thereof together to form first and second layers of the occluding structure. The coupled ends of the occluding structure may define a seam, and the seam may be disposed proximate the distal end of the tubular structure.

In still further embodiments, a vascular device may be provided for placement in a body lumen, where the vascular device includes a proximal end and a distal end. The vascular device may include a tubular structure comprising an inner layer and an outer layer, and the tubular structure may comprise braided metal strands. The vascular device may further include an occluding structure comprising a first layer and a second layer disposed between the inner and outer layers of the tubular structures, wherein the occluding structure is independent of the tubular structure, and wherein the occluding structure comprises a polymer material.

In some cases, the first and second layers of the occluding structure may form a continuous structure via a coupling of free ends of the occluding structure. The coupled ends of the occluding structure may define a seam, and the seam may be disposed proximate the distal end of the tubular structure.

The vascular device may be configured to move between a contracted state when constrained within a delivery device and an expanded state when deployed from the delivery device for delivery to a target site within the body lumen. The inner layer of the tubular structure may comprise a first pick count, as braided, and the outer layer of the tubular structure may comprise a second pick count, as braided, where the relationship between the reduction in diameter and the elongation of the inner layer is substantially the same as the relationship between the reduction in diameter and the elongation of the outer layer as the vascular device is moved between an expanded state and a contracted state. The tubular structure may comprise a leading edge at a transition between the first pick count and the second pick count, and the leading edge may be disposed proximate the distal end of the vascular device when the vascular device is in the expanded state. In some cases, the leading edge may be disposed in an interior of the vascular device when the vascular device is in the contracted state, and the leading edge may be configured to move toward the distal end as the vascular device is deployed from the delivery device.

In still other embodiments, a method of making a vascular device for placement in a body lumen is provided, where the method includes braiding a tubular structure including a proximal portion and a distal portion; folding the tubular structure onto itself such that a surface of the proximal portion of the tubular structure is adjacent a surface of the distal portion of the tubular structure to form an inner layer and an outer layer; folding an occluding structure onto itself, wherein the occluding structure is independent of the tubular structure; and placing the occluding structure between the inner and outer layers of the tubular members.

In some cases, the method further includes coupling ends of the occluding structure together to form first and second layers of the occluding structure. The coupled ends of the occluding structure may define a seam, and the seam may be disposed proximate the distal end of the tubular structure. The method may further comprise attaching the occluding structure to at least one of the inner layer or the outer layer of the tubular structure to hold the occluding structure in place.

In some embodiments of the method, the proximal portion of the tubular structure may define a first pick count and the distal portion of the tubular structure may define a second pick count, wherein the first pick count, as braided, is different from the second pick count, as braided. In addition, the relationship between the reduction in diameter and the elongation of the inner layer may be substantially the same as the relationship between the reduction in diameter and the elongation of the outer layer as the vascular device is moved between an expanded state and a contracted state. The step of folding the tubular structure onto itself may comprise defining a leading edge at a transition between the first pick count and the second pick count.

BRIEF DESCRIPTION OF THE DRAWINGS

The foregoing features and advantages of embodiments of the invention will become apparent to those skilled in the art from the following detailed description of a preferred embodiment, especially when considered in conjunction with the accompanying drawings in which like numerals in the several views refer to corresponding parts.

FIG. 10 is a schematic illustration of a distal portion of a delivery device for delivering a vascular device according to an exemplary embodiment;

FIGS. 11A-11D illustrate deployment of a vascular device from the distal portion of the delivery device of FIG. 10.

DETAILED DESCRIPTION

Embodiments of the present invention now will be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

As described in greater detail below, one embodiment of a vascular device generally includes a tubular structure comprising an inner layer and an outer layer, as well as an occluding structure disposed between the inner and outer layers. The vascular device may be configured to move between a contracted state when constrained within a delivery device and an expanded state when deployed from the delivery device for delivery to a target site within the vessel lumen. In some cases, the inner and outer layers may have free ends proximate a proximal end of the vascular device and may be continuous at a distal end of the vascular device (e.g., the tubular structure may be everted or inverted to create the inner and outer layers). Furthermore, the tubular structure may include a leading edge at a transition between a first pick count and a second pick count, and the device may be configured such that the leading edge is disposed at the distal end of the vascular device when the vascular device is in the expanded state. The leading edge is configured to provide for accurate delivery to a target site and proper fixation to the luminal wall. In addition, the leading edge contributes to a low profile of the vascular device, especially near the distal end of the vascular device.

In still other embodiments, as described below, the occluding structure, which is between the inner and outer layers of the tubular structure, may include a first layer and a second layer. The first and second layers may form a continuous structure (e.g., the polymer fabric may be everted or inverted to create the first and second layers). Moreover, free ends of the occluding structure may be fused together to create the closed structure. In this way, any loose ends may be sealed so as to prevent unraveling and/or shifting of the polymer fabric within the inner and outer layers of the tubular structure.

Figure 1A:
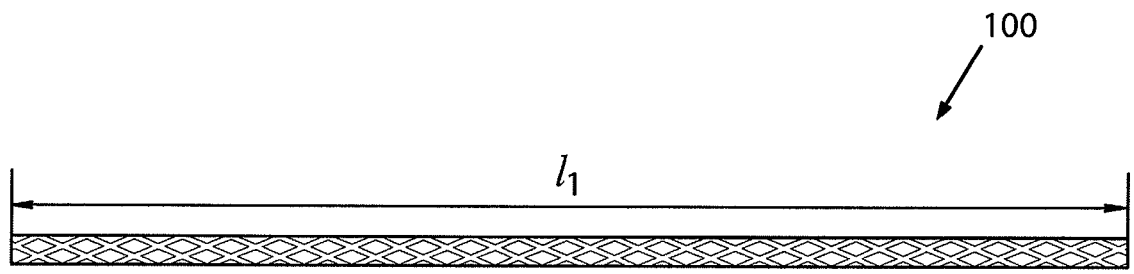
FIG. 1A is a schematic illustration of a vascular device in a contracted state according to an exemplary embodiment.
Figure 1B:
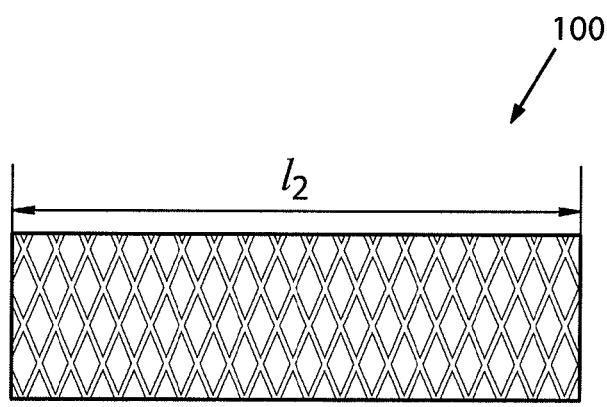
FIG. 1B is a schematic illustration of a vascular device in an expanded state according to an exemplary embodiment.

In general, a stent, graft, or stent-graft, such the vascular device 100 depicted in FIGS. 1A and 1B according to one embodiment, has a contracted state (FIG. 1A) defining a length $l_1$ when constrained within a delivery device (such as a catheter) and an expanded state (FIG. 1B) defining a length $l_2$ when deployed from the delivery device for delivery to a target site within the body lumen (e.g., the site of an aneurysm). For example, a vascular device having a predetermined shape may be collapsed by longitudinally stretching the vascular device (as illustrated in FIG. 1A) for inserting the device into the lumen of a delivery device (e.g., a guide catheter or delivery sheath). The delivery device may then be positioned and advanced in a patient's body such that the distal end of the delivery device is adjacent to the target site. The vascular device may be advanced through the delivery device such that the distal end of the vascular device is near the distal end of the delivery device. Thus, as the vascular device 100 is deployed from the distal end of the delivery device, the diameter of the vascular device self-expands and draws the ends of the device closer to each other. In other words, the overall length $l_2$ of the vascular device when it is in an expanded state (e.g., deployed from the delivery device) is shorter than the overall length $l_1$ of the vascular device when it is in a contracted state (e.g., undeployed from the delivery device).

It is understood that the use of the term "target site" is not meant to be limiting, as the vascular device may be configured to treat any target site, such as an abnormality, a vessel, an organ, an opening, a chamber, a channel, a hole, a cavity, or the like, located anywhere in the body. The term "vascular abnormality," as used herein is not meant to be limiting, as the vascular device 100 may be configured to bridge or otherwise support a variety of vascular abnormalities. For example, the vascular abnormality could be any abnormality that affects the shape of the native lumen, such as an aneurysm, a lesion, a vessel dissection or a tumor. Embodiments of the vascular device may be useful in the vessels of a patient's thoracic area. Furthermore, the term "lumen" is also not meant to be limiting, as the vascular abnormality may reside in a variety of locations within the vasculature, such as a vessel, an artery, a vein, a passageway, an organ, a cavity, or the like. For ease of explanation, the examples used herein refer to an aneurysm. Furthermore, the term "vascular device" is used herein to describe a braided, self-expanding stent or a graft incorporating a self-expanding stent as a structural component.

Once the delivery device is in position at the target site, the vascular device may be urged through the delivery device and out the distal end of the delivery device, whereupon it may substantially return to its expanded state (as illustrated in FIG. 1B). The delivery device may then be removed from the patient's body, leaving the vascular device positioned at the target site.

Figure 2:
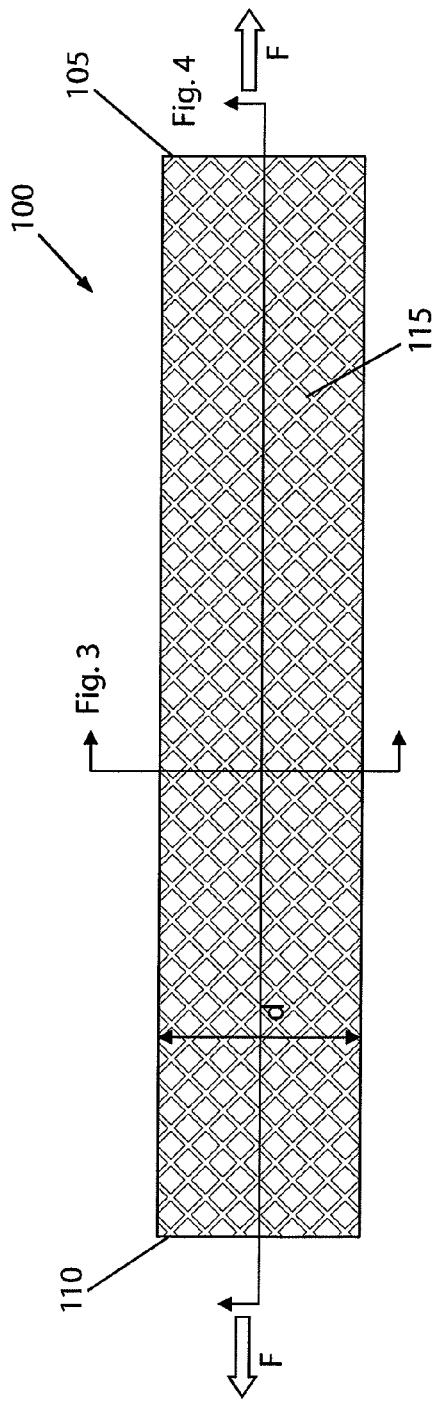
FIG. 2 is an illustration of a vascular device according to an exemplary embodiment.

Referring to FIG. 2, the vascular device 100 defines a proximal end 105 and a distal end 110 in the contracted state and in the expanded state, as well as in states in between the contracted and expanded states (e.g., in the process of being deployed from a delivery device, when, for example, part of the vascular device is in the contracted state within the delivery device and part of the vascular device is in the expanded state outside of the delivery device). As used herein, the term "proximal" refers to a part of the vascular device 100 or the delivery device 250 that is closest to the operator, and the term "distal" refers to a part of the vascular device or the delivery device that is farther from the operator at any given time as the vascular device is being delivered through the delivery device.

As noted above, the vascular device 100 may be configured to be moved between a contracted state and an expanded state. For example, in FIG. 1A the vascular device 100 is shown in a contracted state, whereas in FIG. 1B, the vascular device is shown in an expanded state. The vascular device 100 may be in the contracted state, for example, when the ends 105, 110 of the device are pulled away from each other and/or a radial constraint is applied to the device. In other words, as shown in FIG. 2, the application of a tensile force F on the ends of the device 100 may serve to collapse the outer diameter d of the device such that it may be received within a lumen of a delivery device in the contracted state for delivery to the target site. Thus, in this example, the delivery device (e.g., a catheter) applies the radial constraint to maintain the vascular device 100 in the contracted state.

The vascular device 100 may be configured, however, such that, when the radial constraint is removed, the device can self-expand to the expanded state shown in FIG. 1B. For example, as the vascular device 100 is unsheathed from the delivery device, portions of the vascular device that are no longer constrained by the delivery device may self-expand and freely return to the expanded state, and once the vascular device has been fully deployed from the delivery device proximate the target site, the vascular device will at least partially assume the expanded state. For example, the vessel diameter may limit complete return to the expanded state.

Figure 3:
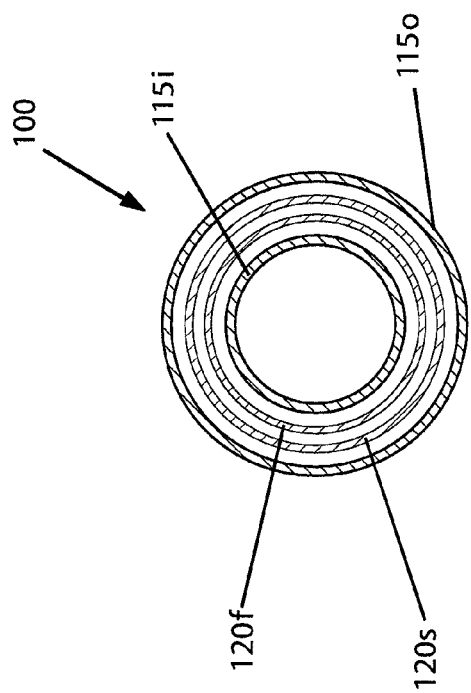
FIG. 3 is a transverse cross-section of the vascular device of FIG. 2.
Figure 4:
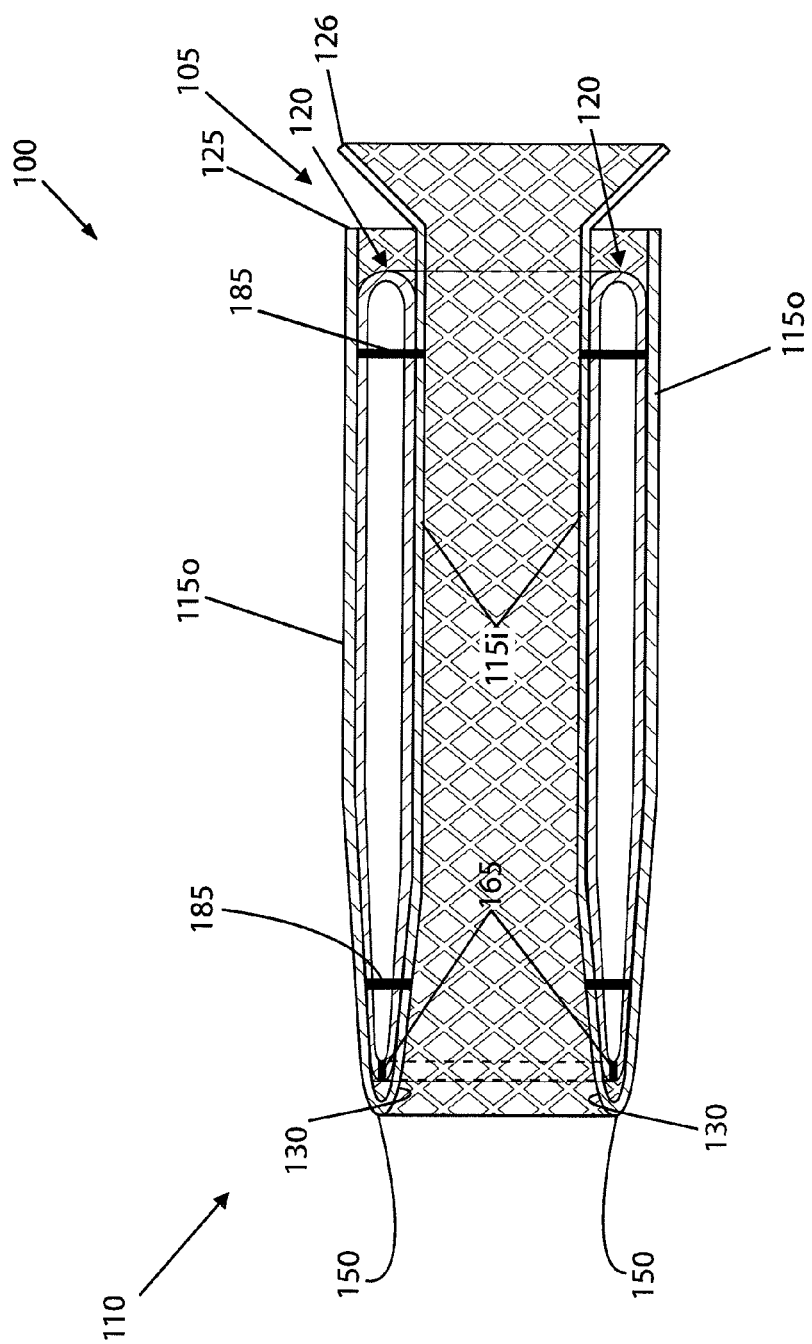
FIG. 4 is an axial cross-section of the vascular device of FIG. 2.
Figure 5:
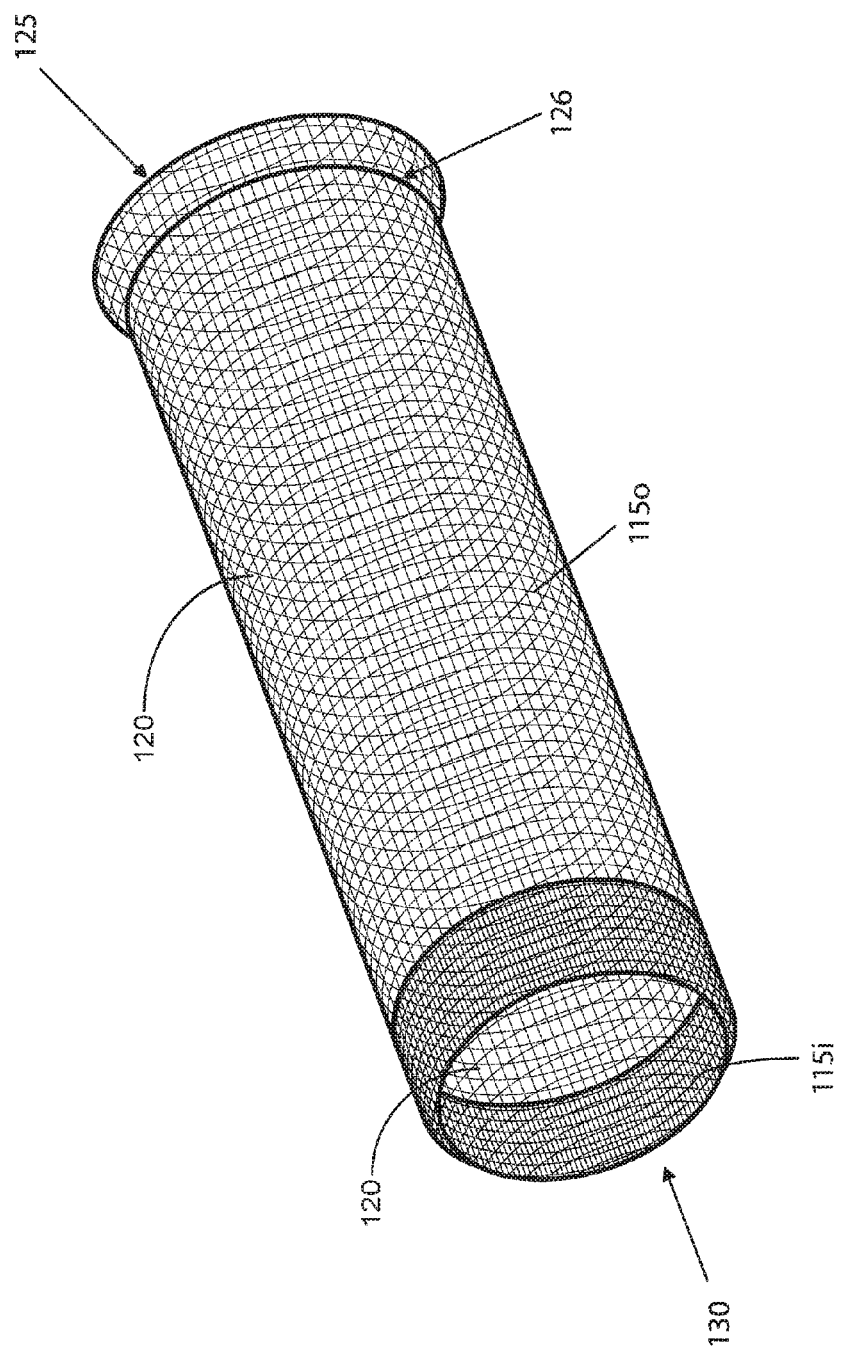
FIG. 5 is a perspective view of a vascular device in an expanded state according to an exemplary embodiment.

In this regard, and with reference to FIGS. 3, 4, and 5, embodiments of the vascular device 100 may comprise a tubular structure 115 and an occluding structure 120. The tubular structure 115 may be configured to have properties that allow the vascular device 100 to self-expand from the contracted state to the expanded state. Such properties, for example, may be imparted through proper selection of the materials for making the device as well as through the manufacturing process.

The tubular structure 115, in some cases, may be formed by braiding, interweaving, knitting, or otherwise combining filamentary materials together, such as by using a conventional braiding machine. These filamentary materials may include, for example, fibers, thread, yarn, cable, metallic wires, polymer monofilament or multifilament strands, and combinations of these materials, any of which are referenced herein as "strands," and such terms may be used interchangeably. The strands may be comprised of any material, such as natural materials, polymers, metals, metallic alloys, or combinations of the same. In some applications, wire strands may be used. The wire strands may be formed of a material that is both resilient and can be heat treated to stabilize the tubular structure 115 (e.g., to substantially set a desired shape or braid pattern). The braid of the tubular structure 115 may be chosen to have a predetermined pick and pitch to define openings or fenestrations so as to vary the impedance of blood flow therethrough.

With respect to vascular devices, where it is important for the device to be delivered to a target site in the body in a reduced profile configuration and subsequently allowed to self-expand after being released from the constraint, stainless steel, other metallic alloys, highly elastic alloys, and/or shape memory alloys may be used that are both resilient and can be heat treated to substantially set a desired shape. Exemplary suitable materials may include, for example, cobalt-based low thermal expansion alloys referred to as Elgiloy® Co—Cr—Ni alloy, nickel-based high temperature high-strength "superalloys" (for example, alloys commercially available from Haynes International under the trade name Hastelloy® alloy), nickel-based heat treatable alloys (for example, alloys commercially available from International Nickel under the trade name Incoloy® alloy) and a number of different grades of stainless steel.

In some embodiments, a factor in choosing a suitable material for the strands is the ability of the strands to retain a suitable amount of the deformation induced by the molding surface when subjected to a predetermined heat treatment, such as is exhibited by shape-memory alloys. One type of shape memory alloy is nickel-titanium (NiTi) alloy, called Nitinol alloy, which is also very elastic. In vascular device applications, for example, this elasticity may allow a self-expanding vascular device to return to a preset expanded configuration from a contracted configuration once it is deployed from a delivery device and is no longer constrained. Accordingly, in some embodiments, at least some of the strands comprise a shape memory alloy. Other materials having elastic properties may also be used, such as spring stainless steel and alloys such as Elgiloy®, Hastelloy®, Phynox®, MP35N®, and CoCrMo alloys.

In some instances, polymeric materials may also be used for the strands. Furthermore, polymeric materials may be combined with other materials in the formation of tubular structures for certain applications. For example, the tubular structure may include a combination of polyamide tubing and stainless steel wire. In other cases, materials may be used that are compatible with magnetic resonance imaging (MRI), considering that some materials may generate heat or experience torque as a result of undergoing MRI or may distort the MRI image. Thus, metallic and/or non-metallic materials that reduce or eliminate the potential problems resulting from the use of MRI may be used, depending on the application.

Further examples of materials and manufacturing methods for vascular devices with shape memory properties are provided in U.S. Publication No. 2007/0265656 titled "Multi-layer Braided Structures for Occluding Vascular Defects" and filed on Jun. 21, 2007, which is incorporated by reference herein in its entirety.

Referring again to FIGS. 3, 4, and 5, the tubular structure 115 may include an inner layer 115*i* and an outer layer 115*o*. In some embodiments, each of the inner and outer layers 115*i*, 115*o* has a free end 125, 126, and the inner and outer layers may be continuous at an opposite end 130 of the tubular structure 115. For example, turning to FIG. 6, the tubular structure 115 may be initially braided defining a proximal portion 135 and a distal portion 140. The tubular structure 115 may be folded onto itself, as shown by the arrows A, such that the outer surface 136 of the proximal portion 135 is adjacent the inner surface 141 of the distal portion 140 to form the inner layer 115*i* and the outer layer 115*o*. In other words, the tubular structure 115 may be everted, such that the distal portion 140 forms the outer layer 115*o* (as shown in FIG. 6), or the tubular structure 115 may be inverted, such that the distal portion forms the inner layer 115*i* (not shown).

In some embodiments, the pick count, or the number of strand crossings per unit length of the braided tubular structure (i.e., along a longitudinal axis X), may be set at one predetermined value for braiding the proximal portion 135 and may be changed to a different predetermined value for braiding the distal portion 140. The pick count for braiding each portion of the tubular structure may be changed in various ways, as known in the art in light of this disclosure. For example, for a given rate of spool carrier movement by the braiding machine, the pick count can be increased by increasing the number of strands being braided or by slowing the axial speed of the mandrel onto which the strands are being braided (i.e., the movement of the mandrel along the longitudinal axis X). Alternatively, the rotational speed of movement of a fixed number of carriers may be increased relative to the axial speed of the mandrel.

Figure 6A:
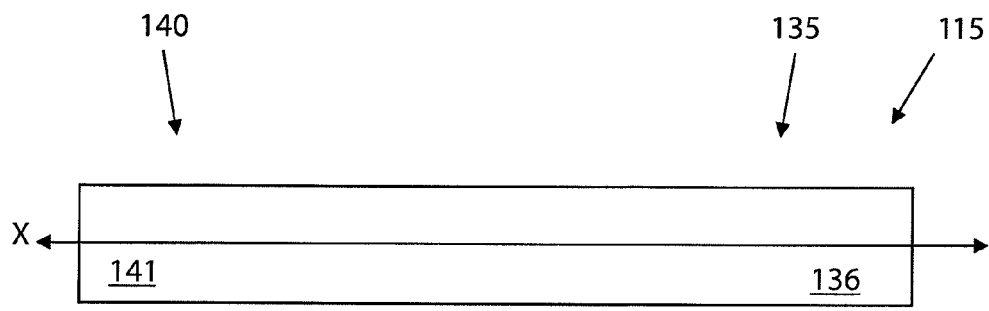
FIGS. 6A-6C illustrate eversion of a tubular structure according to an exemplary embodiment.
Figure 6B:
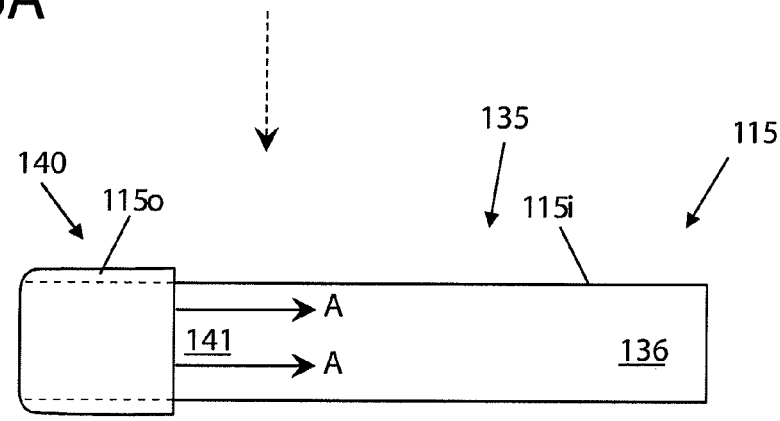
Figure 6C:
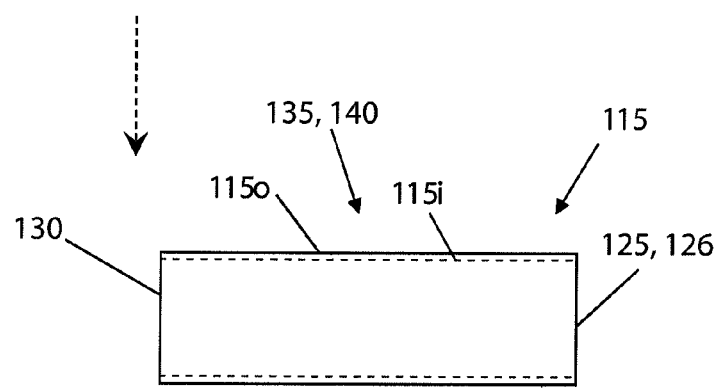
Figure 7:
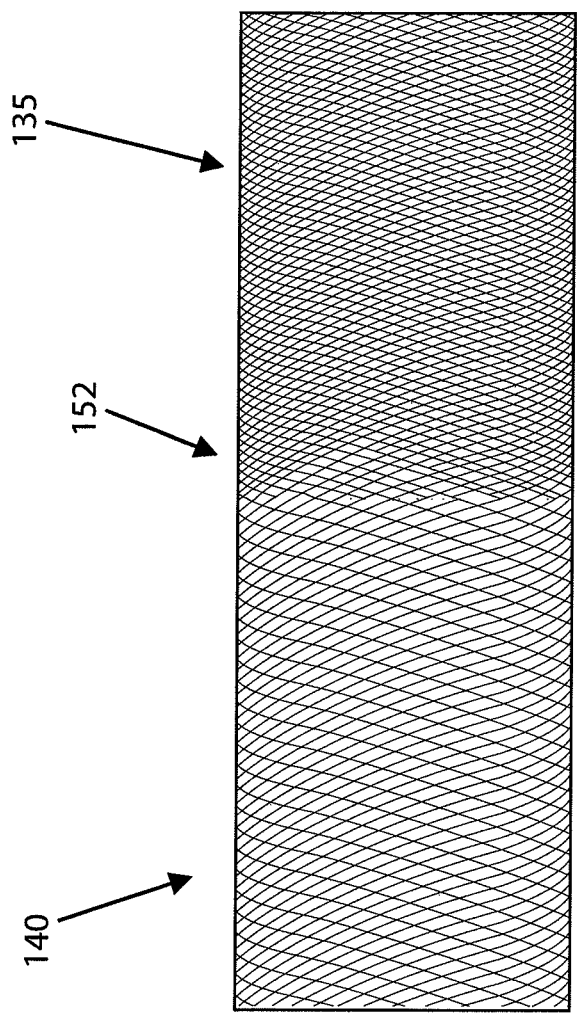
FIG. 7 is a schematic illustration of the tubular structure showing different pick counts in a proximal portion and a distal portion according to an exemplary embodiment.

Thus, with reference to FIGS. 6A-7, the tubular structure 115 may be braided such that the proximal portion 135 has a first pick count and the distal portion 140 has a second pick count. In one embodiment, for example, one of the first and second pick counts may be set at a value in the range of 25-34 PPI (picks per inch), whereas the other of the two pick counts may be set at a value in the range of 38-46 PPI. As shown in FIG. 7, the proximal portion 135 may have a higher pick count than the distal portion 140. When a compression force is applied to the ends of the braided tubular structure (prior to inversion or eversion), the portion of the tubular structure 115 having a lower pick count expands to a larger diameter than the portion having a higher pick count. This is because the portion with the lower pick count has the ability to expand to a larger diameter when compressed than the portion with the higher pick count. Thus, for example, when the first pick count (proximal portion 135) is higher than the second pick count (distal portion 140), the diameter of the distal portion is larger than the diameter of the proximal portion when the compression force is applied, thereby enabling the folding over of the tubular structure 115 as shown in FIGS. 6A-6C.

Depending on which of the first and second pick counts is higher, either inversion or eversion of the distal portion 140 is facilitated, and a leading edge 150 is created at a transition 152 between the first and second pick counts once the braided tubular structure has been folded onto itself (everted or inverted). Accordingly, in some embodiments, the continuous end 130 of the tubular structure may have a leading edge 150 disposed at the distal end 110 of the vascular device 100 when the device is in the expanded state, as illustrated in FIGS. 4 and 5, and the leading edge 150 may be defined by the transition 152 (shown in FIG. 7) between the first and second pick counts.

Said differently, when the first pick count (e.g., proximal portion 135) is higher than the second pick count (e.g., distal portion 140), eversion of the braided tubular structure 115 is facilitated such that the proximal portion forms the inner layer 115*i*. As a result, after the tubular structure has been everted to form the vascular device 100, the inner layer 115*i* may comprise the first pick count, and the outer layer 115*o* may comprise the second pick count. Conversely, when the first pick count (e.g., proximal portion 135) is lower than the second pick count (e.g., distal portion 140), inversion of the braided tubular structure 115 is facilitated, such that the distal portion forms the inner layer 115*i*. As a result, after the tubular structure has been inverted to form the vascular device 100, the outer layer 115*o* may comprise the first pick count, and the inner layer 115*i* may comprise the second pick count. In either case, due to the transition between the first and second pick counts, a leading edge 150 is formed at the transition 152, proximate the distal end 110 of the vascular device 100, once the tubular structure has been folded over to form the inner and outer layers 115*i*, 115*o*.

In the expanded state, the inner layer 115*i* and the outer layer 115*0* may be heat set at the transition 152 to memorize predetermined, expanded state (everted or inverted) diameters. A shim may be placed between the inner and outer layers 115*i*, 115*o*, during the heat setting process, where the shim has a thickness that approximates the thickness of an occlusive structure that later may be placed between the inner and outer layers of the tubular structure 115. The heat setting mold may also have surfaces for shaping a taper at the proximal end and/or the distal end of the tubular structure 115.

Although the first pick count, as braided, is different from the second pick count, as braided, the first and second pick counts may be selected such that the relationship between the reduction in diameter and the elongation for each layer (inner 115*i* and outer 115*o*) is substantially the same once the tubular structure has been folded over onto itself (FIG. 6C). For example, a ratio of the decrease in diameter of the inner layer 115*i* to the increase in length of the inner layer 115*i* may be substantially the same as a ratio of the decrease in diameter of the outer layer 115*o* to the increase in length of the outer layer 115*0*. Thus, adjacent portions of the inner and outer layers 115*i*, 115*o* may remain in their relative adjacent positions as the tubular structure 115 moves between the expanded and contracted states. In this way, the inner layer 115*i* and the outer layer 115*o* of the vascular device may cooperatively collapse and expand at generally the same rate, which enhances the stability of the vascular device and facilitates its delivery into the vessel lumen and subsequent self-expansion.

Figure 8A:
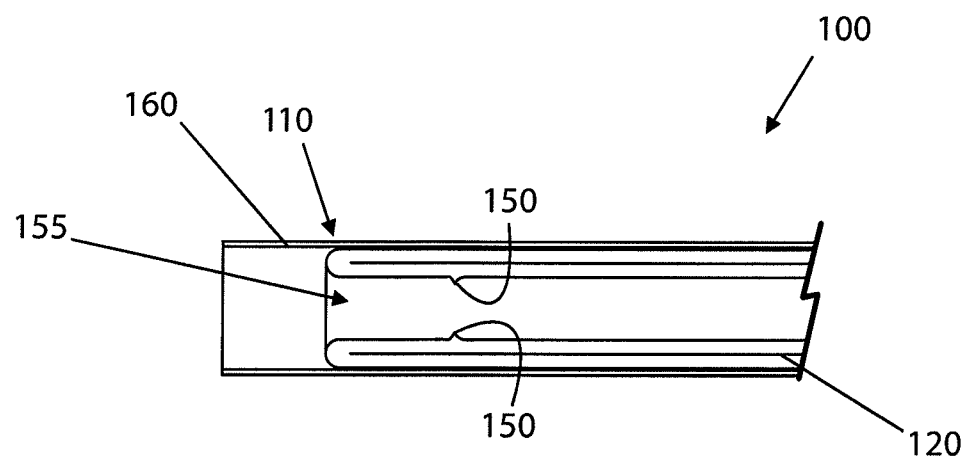
FIGS. 8A-8C illustrate deployment of a vascular device having a leading edge from a delivery sheath according to an exemplary embodiment.
Figure 8B:
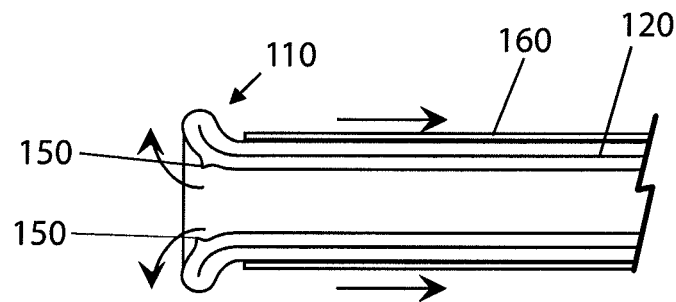
Figure 8C:
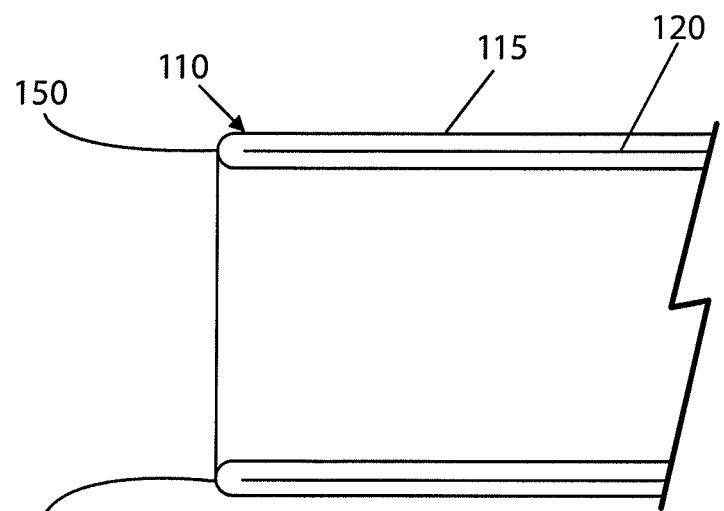

In some embodiments, the position of the leading edge 150 may change as the vascular device 100 is moved from the contracted state to the expanded state (e.g., in the course of deployment from the delivery device). For example, referring to FIGS. 8A-8C, the leading edge 150 may be disposed within an interior 155 of the vascular device 100 as loaded in the delivery device sheath 160 in the contracted state (FIG. 8A), but may roll outward as the sheath is retracted (FIG. 8B) to uncover the vascular device such that, once deployed, the leading edge is disposed at the distal end 110 of the vascular device in the expanded state (FIG. 8C).

As noted above, the difference in pick count, as braided, facilitates the fold over of the inner and outer layers 115*i*, 115*o* of the tubular structure and gives rise to the creation of a leading edge 150 proximate the distal end 110 of the vascular device 100. In other words, the leading edge 150 is created at or in the vicinity of the distal end 110 of the vascular device. The leading edge 150, in turn, makes it possible for the inner and outer layers 115i, 115o to lie in close proximity to one another, spaced apart only by the thickness of any occlusive structure therebetween, which allows the vascular device 100 to have a low profile during delivery through a small-diameter delivery device. Furthermore, without a leading edge 150 at the transition 152, the distal end 110 would have a rounded configuration, creating a gap between the inner and outer layers 115i, 115o and potentially causing blood flow leakage and reduced retention force in the expanded state within the vessel. Thus, in some embodiments, the leading edge 150 may promote secure attachment of the vascular device to the vessel wall and minimize the risk of dislodgement.

In some embodiments, the distal and/or proximal ends of the vascular device may be flared inward or outward. A flare may, for example, aid in the self-expansion of the vascular device, and an outward flare may allow the respective portion of the vascular device to place a greater external pressure upon the vessel, so as to more firmly engage with the vessel wall, again reducing the likelihood of migration of the vascular device. Moreover, in some embodiments, the flare imparted to the proximal end is more prominent than the flare at the distal end. In FIG. 5, only the proximal end of the inner layer 115i is flared outward.

As noted above, in some embodiments, the vascular device 100 may include an occluding structure 120 disposed between the inner and outer layers 115i, 115o, as shown in FIGS. 3-5. The occlusive structure 120 may include one or more layers of occlusive material, which may be any material that is configured to enhance the impedance of blood flow through the vascular device so as to facilitate thrombosis and endothlialization. As used herein, "substantially preclude or impede flow" shall mean, functionally, that blood flow may occur for a short time, e.g., about 5 minutes to 48 hours, through the occlusive material, but that the body's clotting mechanism or protein or other body deposits on the strands of the occluding structure 120 and/or the tubular structure 115 results in occlusion or flow stoppage after this initial time period. For instance, occlusion may be clinically represented by injecting a contrast media into the upstream lumen of the vascular device and if no contrast media flows through the wall of the vascular device after a predetermined period of time as viewed by fluoroscopy, then the position and occlusion of the vascular device is adequate. Moreover, occlusion of the vascular abnormality (e.g., the aneurysm) could be assessed using various echo modalities.

Figure 9A:
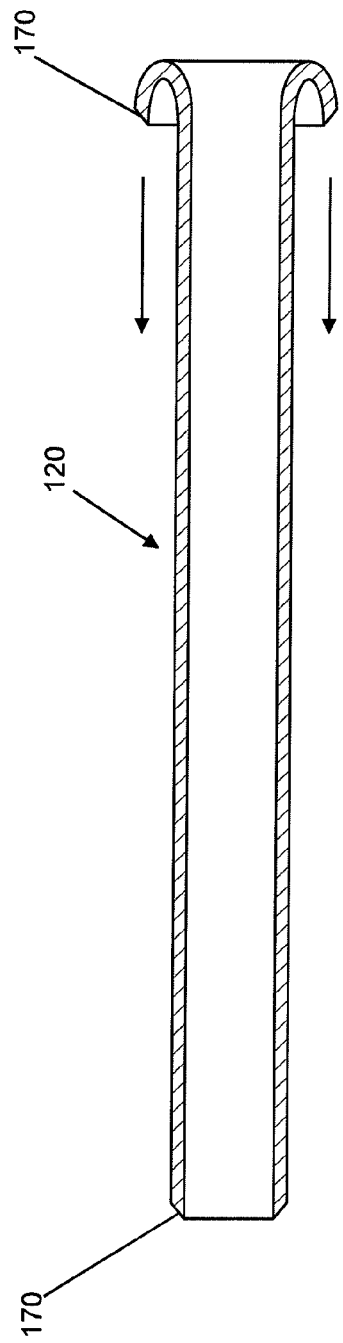
FIGS. 9A-9B illustrate eversion of an occluding material to form an occluding structure according to an exemplary embodiment.
Figure 9B:
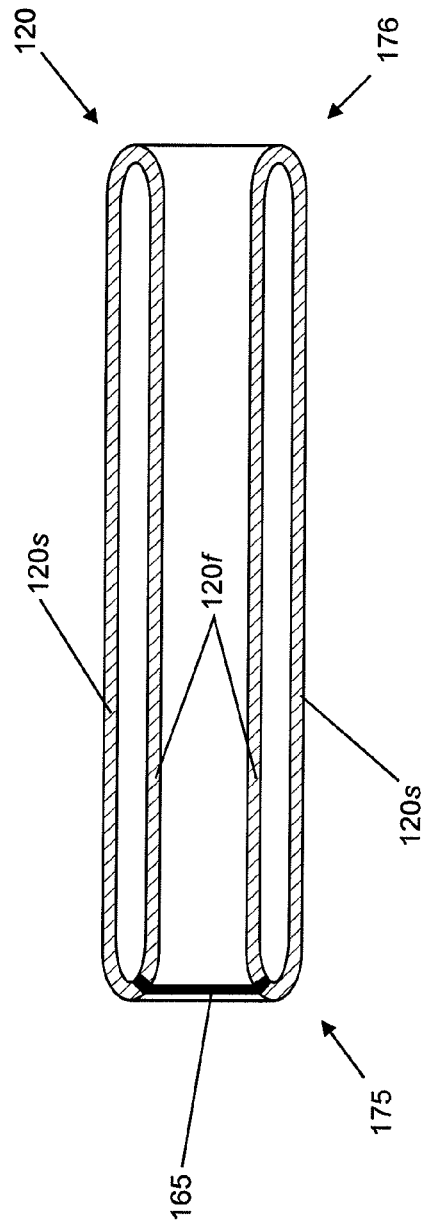

Turning to FIGS. 4, 9A, and 9B, in some embodiments, the occluding structure 120, which may be tubular in shape to correspond to the shape of the tubular structure 115, may include a first layer 120f and a second layer 120s disposed between the inner and outer layers 115i, 115o of the tubular structure. The first and second layers 120f, 120s may form a continuous structure via a coupling (e.g., a single seam 165) that joins together free ends 170 of the structure. In this regard, and similar to the tubular structure 115, the occluding structure 120 may be formed by initially braiding strands onto a mandrel to achieve a tubular configuration. In some embodiments, for example, the occluding structure 120 may be made of 135 denier, 34 filament polyester yarn. The occluding structure may then be folded onto itself (inverted or everted) as shown in FIG. 9A, and the free ends 170 of the material may be coupled together to form the continuous occluding structure 120. Thus, the coupled ends of the occluding structure 120 may define a circumferential seam 165.

The free ends 170 may be coupled together through melting, heating, bonding, or other processes for joining the two ends to form the continuous occluding structure 120. For example, in some cases, the seam 165 may be a weld, such as a hot wire melted weld, effectively sealing a volume created between the first and second layers 120f, 120s. Thus, through such coupling of the free ends 170, fraying and/or unraveling of the occluding material that may otherwise occur at the free ends (and any particulate generation that may result from this fraying and/or unraveling) may be avoided. In addition, the risk of the occluding structure 120 becoming dislodged from or shifting positions within the tubular structure 115 may be minimized.

To further reduce the risk of dislodgment or shifting of the occluding structure 120 within the tubular structure 115, the occluding structure may be attached to at least one of the inner and outer layers 115i, 115o. For example, the occluding structure 120 may be held in place between the inner and outer layers 115i, 115o of the tubular structure through the use of sutures 185 or other suitable attachment methods, as illustrated in FIG. 4. In some cases, the sutures 185 may be made using radiopaque filament thread, such as platinum iridium thread, to allow a medical practitioner to view the location of the vascular device 100 within the body using radio fluoroscopy to facilitate proper delivery and positioning of the device. For example, the first and second layers 120f, 120s of the occluding device may be sutured to the inner layer 115i of the tubular device, if desired, as shown in FIG. 4.

Although the occluding structure 120 is depicted in the figures as elliptical for the purposes of explanation (i.e., with a gap between the first and second layers 120f, 120s in the illustrated cross-sectional views), the occluding structure may actually be flattened between the inner and outer layers 115i, 115o of the tubular structure due to the outward forces exerted by the inner and outer layers in both the contracted state (in which case the forces are directed towards the walls of the delivery sheath) and the expanded state (in which case the forces are directed towards the walls of the vessel near the target site). The seam 165 may be positioned anywhere along the length of the occluding structure 120. For example, in some cases, the seam 165 may be positioned near the distal end 175 of the occluding structure 120, as shown in FIG. 9.

Furthermore, the occluding structure 120 may extend, in some embodiments, substantially from the distal end 110 of the vascular device (e.g., the end 130 of the tubular structure 115) substantially to the proximal end 105 (e.g., the free ends 125, 126), as illustrated in FIG. 4. In this way, the gap between the continuous end 130 of the tubular structure 115 and the corresponding end 175 of the occluding structure 120, as well as between the most proximal portion of the tubular structure and the corresponding end 176 of the occluding structure, can be minimized, thereby providing greater occlusive properties in these areas (e.g., around the occluding structure).

In some embodiments, the occluding structure 120 may be braided using strands that consist of or include polymer material. For example, the occluding structure 120 may be made of polyester fabric. In addition, other parameters may be selected and/or manipulated to maximize the occluding properties of the occluding structure 120.

Furthermore, the helix angle of the strands (e.g., the angle formed between the strand and the longitudinal axis of the braid mandrel as the strand is applied to the mandrel) used to braid the tubular structure 115 may be selected such that, once inverted or everted, the helix angles of the inner and outer layers 115i, 115o are generally aligned, allowing the inner and outer layers to move together as the vascular device 100 is contracted and expanded (i.e., contracting and expanding approximately to the same extent). In this regard, the occluding structure 120 may also be braided such that, once inverted or everted and fused to form a continuous structure, the helix angles of the occluding structure may be substantially aligned with the helix angles of the inner and outer layers 115*i*, 115*o* of the tubular structure. Such uniform movement reduces the risk of bunching or gathering of the occluding structure 120 within the tubular structure 115, which would otherwise reduce the effectiveness of vascular device 100 by increasing its delivery profile and/or generating gaps between the various layers of material that may cause leaks.

The occluding structure 120 may further be configured to have the same or similar pick count as one or both of the inner and outer layers of the tubular structure 115*i*, 115*o*. For example, in some embodiments, the pick count of the occluding structure 120 may be selected to correspond to the pick count of a section of the inner and outer layers 115*i*, 115*o* of the tubular structure, such as by being a multiple of (e.g., double) the pick count of the outer layer 115*o*. In other words, the tubular structure 115 in this example may be braided using 72 strands, whereas the occluding structure 120 may be braided using 144 strands. In this way, the helix angle of the strands comprising the occluding structure 120 may align with (i.e., be similar to) the helix angle of the strands that make up the inner and outer layers 115*i*, 115*o*. Similarly, other parameters of the tubular structure 115 and the occluding structure 120, including pick count, strand diameter, braid mandrel diameter, number of strands, filament material and composition, and helix angle, may be selected to enhance the cooperation between the occluding structure and the tubular structure or to otherwise impart desirable properties to the vascular device.

In some cases, the vascular device 100 may be specifically configured to work with and/or be deployed by a certain type of delivery device. For example, embodiments of a delivery device for delivering a vascular device to a target site within the human body are described in application Ser. No. 13/236, 803, filed concurrently herewith, the contents of which are hereby incorporated by reference herein. In the referenced delivery device, a distal portion 200 (depicted in FIG. 10) may be provided that is configured to retain a proximal end of the vascular device until the vascular device is positioned for deployment at the target site.

For example, with reference to FIGS. 10 and 11A, the proximal end 105 of the vascular device 100 may be retained within a metal sleeve 205 between a free-floating ring 210 and a knub 215 formed at the distal end of a pusher wire 220. A pusher band 225, which may be a portion of increased thickness integral to or fixedly attached to the pusher wire 220 and configured to move with the pusher wire, may be provided to engage the free-floating ring 210 and push the vascular device 100 out of the distal portion 200, as described below. In some cases, as depicted, a second band 235 may be provided on the other side of the free-floating ring 210, such that the movement of the free-floating ring is limited on either side by the bands 225, 235. The distal portion 200 of the delivery device may, for example, be placed within a delivery sheath 250 that is movable with respect to the distal portion 200. Thus, once at the target site, the delivery sheath 250 may be retracted in the direction P shown in FIG. 11B to progressively release the distal part of the vascular device 100. To release the proximal end 105 of the vascular device 100, the pusher wire 220 may be advanced in the direction of the arrow D, as shown in FIG. 11B. When the distal end of the pusher band 225 contacts the proximal surface of the free-floating ring 210, the band and the ring can advance distally together as the pusher wire 220 continues to be moved in the direction of arrow D.

This motion eventually causes the distal surface of the ring 210 to contact the proximal end of the vascular device 100 (shown in FIG. 11C), and continued movement of the pusher wire 220 in the D direction thus pushes the vascular device 100 out of the metal sleeve 205 (shown in FIG. 11D), as the knub 215 (which is attached to and moves with the pusher wire) is no longer restricting the distal opening 230 of the metal sleeve 205. FIGS. 11A-11D illustrate the relative movement of the pusher band 225, free-floating ring 210, and knub 215 with respect to the proximal end of the vascular device 100 and the metal sleeve 205 described above as the pusher wire 220 is advanced in the direction D.

Figure 12:
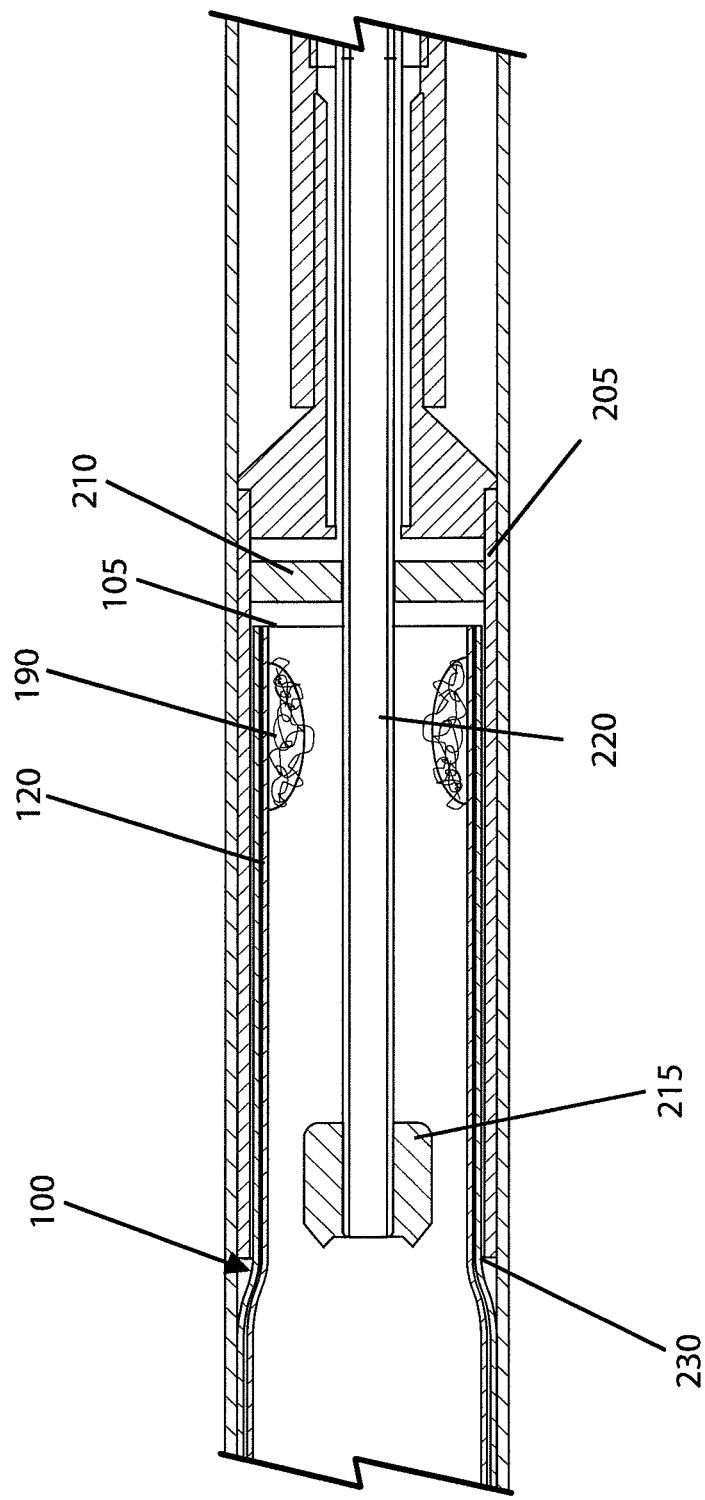
FIG. 12 is a schematic illustration of a vascular device with an occluding structure having a section of increased thickness positioned within a distal portion of a delivery device according to an exemplary embodiment.

Referring to FIG. 12, the occluding structure 120 of the vascular device 100 may include a section of increased thickness 190 that is configured to maintain the vascular device within the delivery device (e.g., the distal portion 200 of the delivery device shown in FIG. 10) while the proximal end 105 of the vascular device 100 is positioned between the free-floating ring 210 and the knub 215. In another embodiment, the section of increased thickness may be part of the tubular structure 115, rather than the occluding structure 120. Regardless, the increased thickness 190 may be configured such that the section 190 cannot pass out of the distal opening 230 of the metal sleeve 205 until such time that the knub 215 has been pushed clear of the distal opening 230. In some cases, the area of increased thickness 190 may be a suture (such as suture 185 in FIG. 4) stitched into the occluding device, a marker band for allowing radioscopic monitoring of the location of the end of the marker band, or any other feature that increases a localized thickness of the occluding device near the proximal end of the device.

Accordingly, as described above, a vascular device 100 may be made having a low profile suitable for delivery through a small-diameter delivery device. For example, in some cases, the vascular device 100 may be designed to have a diameter that is less than 19 French, or 19 Fr. (3 Fr. being equivalent to 1 mm). Thus, in some embodiments, vascular devices may be configured having an overall diameter of between 12 and 17 Fr.

This invention has been described herein in considerable detail in order to comply with the Patent Statutes and to provide those skilled in the art with the information needed to apply the novel principles and to construct and use embodiments of the example as required. However, it is to be understood that specifically different devices can carry out the invention and that various modifications can be accomplished without departing from the scope of the invention itself. For example, options shown for one embodiment could easily be applied to other embodiments, as desired for a particular application, without departing from the scope of this invention.

That which is claimed:

1. A vascular device configured to move between a contracted state when constrained within a delivery device and an expanded state when deployed from the delivery device for delivery to a target site within the body lumen, wherein the vascular device includes a proximal end and a distal end, the vascular device comprising:

a tubular structure comprising an inner layer and an outer layer, wherein the inner layer defines a first pick count and the outer layer defines a second pick count, wherein the tubular structure comprises a leading edge at a transition between the first pick count and the second pick count, wherein the inner layer of the tubular structure is continuously braided with the outer layer of the tubular structure, wherein the first pick count, as braided, is different from the second pick count, as braided, and wherein the first and second pick counts are selected such that the relationship between a reduction in diameter and an elongation of the inner layer is substantially the same as the relationship between a reduction in diameter and an elongation of the outer layer as the vascular device is moved between the expanded state and the contracted state.

2. The vascular device of claim 1, wherein the leading edge is disposed proximate the distal end of the vascular device when the vascular device is in the expanded state.

3. The vascular device of claim 1, wherein the leading edge is disposed within an interior of the vascular device when the vascular device is in the contracted state and is configured to move to the distal end as the vascular device is deployed from the delivery device.

4. The vascular device of claim 1, wherein each of the inner and outer layers of the tubular structure comprises a free end proximate the proximal end of the vascular device.

5. The vascular device of claim 1, wherein the first pick count, as braided, is higher than the second pick count, as braided.

6. The vascular device of claim 1 further comprising an occluding structure disposed between the inner and outer layers of the tubular structure, wherein the occluding structure is tubular in shape and comprises a first layer and a second layer disposed between the inner and outer layers of the tubular structure.

7. The vascular device of claim 6, wherein the first and second layers of the occluding structure form a continuous structure via a coupling of free ends of the occluding structure.

8. The vascular device of claim 7, wherein the coupled free ends are disposed adjacent the inner layer of the tubular structure.

9. The vascular device of claim 6, wherein the occluding structure is attached to at least one of the inner layer or the outer layer of the tubular structure.

10. The vascular device of claim 6, wherein the occluding structure comprises a polymer material.

11. The vascular device of claim 6, wherein the occluding structure extends substantially from the distal end of the vascular device substantially to the proximal end of the vascular device.

12. The vascular device of claim 6, wherein the outer layer of the tubular structure includes a section of increased thickness configured to maintain the vascular device within a delivery device prior to deployment.

13. The vascular device of claim 1, wherein, in the expanded state, the inner layer of the tubular structure defines a length that is greater than a length defined by the outer layer of the tubular structure.

14. A vascular device for placement in a body lumen, wherein the vascular device includes a proximal end and a distal end, the vascular device comprising:

a tubular structure comprising an inner layer and an outer layer, wherein the tubular structure comprises braided metal strands, wherein the inner layer of the tubular structure comprises a first pick count, as braided, and the outer layer of the tubular structure comprises a second pick count, as braided, the tubular structure further comprising a leading edge at a transition between the first pick count and the second pick count; and an occluding structure comprising a first layer and a second layer disposed between the inner and outer layers of the tubular structures, wherein the occluding structure is independent of the tubular structure, and wherein the occluding structure comprises a polymer material.

15. The vascular device of claim 14, wherein the first and second layers of the occluding structure form a continuous structure via a coupling of free ends of the occluding structure.

16. The vascular device of claim 15, wherein the coupled ends of the occluding structure define a seam, and wherein the seam is disposed proximate the distal end of the tubular structure.

17. The vascular device of claim 14, wherein the vascular device is configured to move between a contracted state when constrained within a delivery device and an expanded state when deployed from the delivery device for delivery to a target site within the body lumen.

18. The vascular device of claim 17, wherein the relationship between a reduction in diameter and an elongation of the inner layer is substantially the same as the relationship between a reduction in diameter and an elongation of the outer layer as the vascular device is moved between an expanded state and a contracted state.

19. The vascular device of claim 17, wherein the leading edge is disposed proximate the distal end of the vascular device when the vascular device is in the expanded state.

20. The vascular device of claim 14, wherein the leading edge is disposed in an interior of the vascular device when the vascular device is in the contracted state and is configured to move toward the distal end as the vascular device is deployed from the delivery device.

* * * * *